(12) United States Patent
Alfaro Castaneda

(10) Patent No.: US 8,557,225 B2
(45) Date of Patent: Oct. 15, 2013

(54) SOLUTION AND METHOD FOR CLEANING TOOTH ENAMEL

(76) Inventor: Jose Fernando Alfaro Castaneda, Guanajuato (MX)

( * ) Notice: Subject to any disclaimer, the term of this patent is extended or adjusted under 35 U.S.C. 154(b) by 152 days.

(21) Appl. No.: 12/988,968

(22) PCT Filed: Apr. 23, 2009

(86) PCT No.: PCT/MX2009/000037
§ 371 (c)(1),
(2), (4) Date: Oct. 21, 2010

(87) PCT Pub. No.: WO2009/131431
PCT Pub. Date: Oct. 29, 2009

(65) Prior Publication Data
US 2011/0038812 A1 Feb. 17, 2011

(30) Foreign Application Priority Data
Apr. 24, 2008 (MX) .................. MX/A/2008/005299

(51) Int. Cl.
*A61K 8/365* (2006.01)
(52) U.S. Cl.
USPC .......................................... 424/55
(58) Field of Classification Search
None
See application file for complete search history.

(56) References Cited

U.S. PATENT DOCUMENTS

| 5,281,412 A * | 1/1994 | Lukacovic et al. ............. 424/52 |
| 5,310,544 A * | 5/1994 | Alfaro ............................. 424/49 |
| 5,464,608 A | 11/1995 | Khartchenko et al. |
| 2006/0072958 A1 | 4/2006 | Tsaur |
| 2006/0204933 A1 | 9/2006 | Tsaur |

FOREIGN PATENT DOCUMENTS

| CN | 1313081 A | 9/2001 |
| MX | PA03009113 A | 4/2005 |
| MX | PA06002898 A | 5/2006 |

OTHER PUBLICATIONS

International Search Report, PCT/MX2009/000037, (WO 2009/131431), Jul. 3, 2009.

\* cited by examiner

*Primary Examiner* — Brian Gulledge
*Assistant Examiner* — Snigdha Maewall
(74) *Attorney, Agent, or Firm* — Cook Alex Ltd.

(57) ABSTRACT

The invention relates to a solution with a concentration of 6N of HCl, citric acid ($C_6O_7H_8$) and water demineralised by reverse osmosis and bacterially purified by ozonisation and lemon-flavored artificial liquid essence or anise-flavored artificial liquid essence and water demineralised by reverse osmosis and bacterially purified by ozonisation, and to a method for using same to dissolve the brown pigmentation of teeth affected by problems of mottled enamel or chronic endemic dental fluorosis, as well as teeth with white, opaque or yellow stains. The composition is applied to the surface of the part to be treated using a small cotton swab secured with snap clamps, which performs a firm circular rubbing motion until the stains have been removed. Subsequently, a paste comprising calcium hydroxide and water is applied to the part to be treated in order to neutralize any surplus solution and, finally, the mouth is washed with simple water in order to remove any calcium hydroxide residue. In addition, the above-mentioned lemon-flavored or anise-flavored essence leaves a pleasant taste and freshness in the patient's mouth.

7 Claims, No Drawings

SOLUTION AND METHOD FOR CLEANING TOOTH ENAMEL

BACKGROUND TO THE INVENTION

In today's odontology the problem of mottled enamel presents itself with respect to the denture of people of any age and gender. Pigmentation, as well as different stages of this adamantine hypoplasia by fluoride or chronic endemic dental fluorosis, is due to the build-up of interprismatic organic substances which have been abnormally diffused and have remained trapped inside the adamantine defective structure and which later has degraded, thereby causing brown staining so unpleasant to the aesthetic aspects of the person who suffers from this condition.

It is known in the practice of odontology that peroxide applications have been practiced in order to try to solve this problem. However, carrying out peroxide applications have not achieved satisfactory results. Likewise, some mechanical removal methods using abrasives have been carried out, but have not achieved satisfactory results.

Bleaching techniques that have been practiced are time consuming per treatment and require numerous visits to the office of a dental professional. Also, they produce very unsatisfactory results.

According to patent document 163200MX, filed on Feb. 20, 1989, a solution with a 3 N concentration, up to 12 N, of HCl, in distilled water is proposed for use in a procedure for applying this solution exclusively by a dental surgeon or other trained personnel. According to this disclosure, the solution permanently dissolves the brown pigmentation of the teeth affected by problems of mottled enamel or chronic endemic dental fluorosis. Said solution is said to provide satisfactory results even diluted at 50% in distilled water; thus protection within a concentration range of 5.10 N=17.33, of HCl in distilled water, up to a preferred estimated concentration of 18.6 gr. HCl, in 100 ml of distilled water was proposed.

The described procedure in patent document 163200MX consists of isolating the dental pieces to be treated, one by one, with the conventional rubber dam. Subsequently, with a small cotton swab secured with snap clamps, the HCl solution is applied to the surface of the part to be treated, performing a firm circular rubbing motion for approximately two to three minutes, according to the mottle intensity degree. Immediately after dissolving the brown stain, a calcium hydroxide paste of the dental item to be treated is applied (during approximately two minutes), in order to neutralize any acid residual, since the this taste is unpleasant for the patient. Finally, the treated part is rinsed with water several times, in order to remove the excess calcium hydroxide paste.

The mottled enamel or chronic endemic dental fluorosis is a type of adamantine hypoplasia caused by fluoride, and this condition was first described by this terminology in the United States by G. V. Black and Frederick Mc Kay in 1916.

We now know that the intake of fluoride water during the formation of teeth may result in mottled enamel. The mottle intensity increases with the intake of fluoride in the water; accordingly, there will be a slight mottle, with no clinical significance, with levels below 0.9 to 1 part per million of fluoride in water, while it gradually becomes more evident above such level because fluoride is the indirect agent causing mottled enamel. Fluoride belongs to the halogens; halogen means in Greek "salt formers". Fluoride is the most 25 electronegative of the halogens. Halogens are distributed all over the earth's crust and in the seas as very active elements; they are never found in free state in nature.

Fluoride is found in fluorine form, $CaF_2$ and cryolite, $Na_3AR_6$. Fluoride is the indirect cause of mottled enamel, since it only produces the morphological alteration of the enamel prisms and not the mottle's brown stain.

The fluoride metabolism comes from the oral intake of water and food; it then goes to the stomach and intestines and there, by means of absorption, to the bloodstream and other body liquid flow paths and eventually to bones and teeth. The latter ones are where the problem of the presence of mottled enamel has been evaluated, as well as the different stages of this adamantine hypoplasia due to fluoride and chronic endemic dental fluorosis.

The storage of fluoride in calcified tissue is preferably produced in areas of increased metabolic activity within close proximity to flowing liquids; as a result, there is a greater fluoride concentration in the periosteal tissue than in the underlying bone. Thus, the greatest fluoride concentration in the enamel is produced in the outermost portion of its surface, decreasing the fluoride content as it moves forward the inside.

This fluoride concentration gradient has been observed both in not erupted teeth as well as in erupted teeth, in permanent and primary teeth, without taking into consideration the previous exposure to fluoride.

It is thus inferred that the fluoride storage in the enamel during pre-eruptive periods of dental development takes place through two mechanisms:

A) Precipitation of a fluorosubstituted apatite during mineral deposit over the enamel matrix is one mechanism.

The adamantine matrix is damaged, and the ameloblasts suffer disorders during the formation period of dental development having organic matrix interruption, carrying out an apatite period according to the fluoride increase in tap water and food. In this apatite transition period, the fluoride due to its high electronegativity potential starts to release phosphate ions and modify the molecular structure of the enamel, resulting in fluoride ions to be repelled and as a result open the structure, leaving irregular spaces, as well as modifying penta-hexagonal adamantine prisms in irregularly-shaped structures of enamel corpuscles.

B) Another mechanism is consequent modification of interprismatic space, where it normally receives interprismatic organic substances.

More specifically, with the above-mentioned disorder, the interprismatic organic substance is diffused in abnormal quantities following the damaged form of the adamantine structure. As a consequence, the interprismatic organic substance is trapped, subsequently being degraded and giving rise to the unpleasant brown stain, in addition to the enamel's own transparency.

Important Observations

According to the fluoride level in tap water and the apatite transition stage it is going through, there is variety in the intensity of the mottle, including:

1. Alterations that result in white dotting of the enamel.
2. Opaque areas in more than one dental surface.
3. Moderate alterations where there are yellowish areas on the surface.
4. Advanced alterations where there is cavity formation and brown pigmentation on the surface.
5. Severe fluorosis, which includes a corroded aspect of the teeth where the enamel has worn out and has fractured.

Known properties of enamel, including that it is a relatively inert tissue, of high mineralization and hardness which reacts before harmless stimulation, chemical, physical or biological damage, with structural-like loss, are directly related to the cause agent intensity, and the magnitude of these properties directly affects these matters. These properties determine that tooth enamel cannot be regenerated even though it is capable of remineralization. The enamel is a structure which mainly consists of 96% to 98% by weight hydroxyapatite, and the rest is organic content.

At the moment of tooth eruption, the enamel is not fully calcified yet, and it is vulnerable during a post-eruptive period of approximately two years, during which the enamel's calcification continues. During this period, called enamel maturing period, there is a continuous fluoride build-up in the most superficial portions of the enamel. This fluoride comes from the saliva as well as from the teeth's exposure to water. Thus, most of the fluoride inside the enamel is produced during the eruptive period having enamel formation and during the post-eruptive period of the enamel's maturing. In relation to the above, it has been determined there is a better formula of the cleaning solution for the teeth enamel when introducing to the same citric acid, $C_6O_7H_8$, which allows softening, solubility and permeability of the organic matter.

Citric acid owes its acidity to its three carboxylic groups (—COOH), which when in solution lose a proton, transforming into a citrate ion having the ability to control the pH of the acid solutions and to form citrates.

Citric acid as incorporated in the present disclosure is an irrigating substance classified as a chelating agent which, due to its low pH, reacts with the metallic ions in the hydroxyapatite crystals in order to produce a metallic chelating agent which reacts with the chelating agent's terminal groups when removing calcium ions of the dentine, forming a ring. The dentine softens changing the solubility and permeability aspects of the tissue, especially the peritubular dentine, rich in hydroxyapatite, increasing the diameter of the exposed dental tubes. These chelating agent properties also provide a great affinity as thus used due to ferrous alkali characteristics of the dental structure. Also, this chelating agent is naturally found inside the body, thus making it biologically more acceptable than other acids. Citric acid is effective in altering the hydroxyapatite solubility; it has been used in several concentrations, from 0.6 up to 50% by weight. Its effect is very fast and it only requires five seconds to apply a 6% solution over the enamel to remove the undesired dental covering.

This undesired dental covering is of weak adherence structure and it consists of organic and inorganic material. It has been determined that, in order to remove it, a combination of active substances which act upon the inorganic component is required, including chelating agents or acids to remove both components, organic as well as inorganic, an attribute the new composition of this disclosure has for cleaning the teeth enamel. In addition same has the further advantage of subsequently causing the enamel itself to remineralize, resulting in an excellent cleaning improvement. Thus the addition of citric acid results in a significant improvement to our original solution that did not contain same.

The citric acid, due to its ability to remove the undesired dental layer, is not a chemically active substance having antimicrobial effect. Therefore, removing the undesired dark layer also removes microorganisms which are present, allowing cleaning of the enamel.

When the citric acid solution is applied over the surface of the enamel according to this disclosure, it demineralizes and the inorganic matrix of the adamantine prisms or rods dissolves, creating micropores, grooves and/or micrometric cracks from which microorganisms are cleaned away, thus bringing about a more effective and energetic penetration of the HCl solution, which has also been strengthened by the same citric acid making its action much more effective on the teeth enamel, requiring less time to remove the undesired dark dental layer, allowing the HCl solution to immediately act by dissolving not only the brown stain of the mottle, but also the white, opaque or yellow stains. This is all accomplished in under a minute and a half unlike the solution described in patent document No. 163200MX, which needed two to three minutes to act upon the stains, thus reducing treatment time by over half or much more. This also greatly benefits both the patient as well as the dentist or trained personnel since the time needed for their effort and for the patient to be in a treatment posture during treatment is reduced to a very short period of time. Accordingly, by this invention it has been determined that introducing the citric acid to our original solution greatly strengthens its efficacy. In addition, the new teeth enamel cleaning composition is a colorless liquid. Such a composition can be perceived as slightly irritating, with a very sour and acid taste, and the composition can be supplemented with lemon-flavored or anise-flavored essence in order to eliminate the slightly irritating effect and the acidity of HCl (hydrochloric acid) as well as the $C_6O_7H_9$ (citric acid), leaving a pleasant taste and freshness in the patient's mouth.

On the other hand, since there is not an absorption path for this for the human organism, studies and practice have proved that in the application of the solution for cleaning the teeth enamel there is no level of toxicity attendant thereto.

With regard to the application procedure of the solution relating to patent document No. 163200MX, same includes placing the conventional rubber dam dental wax applied in the tooth's neck for sealing the dam and protecting the lower teeth and gingival mucosa, as well as the rest of the oral cavity and treating with the composition of that publication. The present disclosure provides an important improvement in the composition used in the application process.

By way of informing, it is also mentioned that U.S. Pat. No. 5,310,544 dated May, 1994, in which a hydrochloric acid-based cleaning solution of teeth enamel is described at a concentration of 6N. Giving maximum effectiveness is described when dissolving the brown stain of mottle or chronic endemic dental fluorosis in a time between approximately two and three minutes, which at that time was thought to be fully efficient, teaching that the only and exclusive active ingredient was hydrochloric acid.

Likewise, the U.S. Pat. No. 5,464,608, dated Nov. 7, 1995, describes a composition containing citric acid, which is said to confer to the solution the property to give the patient a sense of freshness and a pleasant smell when applying it to the patient's teeth and oral cavity. In regards thereof, we provide and present improved compositions and procedure consisting of both an HCl solution (hydrochloric acid) and $C_6O_7H_8$ (citric acid) in certain optimum percentages. This was not arrived at by an accident or by chance, but rather by the research and work of many years of investigation and tests, which were used to find the appropriate interaction of the optimum percentages of the solution components for cleaning teeth enamel, which shows results that successfully exceed and by significant degrees the effectiveness of the prior art solution since it not only strengthens its effectiveness to dissolve the brown stain of the mottle, but it now also makes white, opaque and yellow stains disappear, all this at half the time needed for the prior solution, whose only active ingredient is HCl (hydrochloric acid). It should be noted that the $C_6O_7H_8$ (citric acid) is not added to the original formula to give a pleasant taste and smell to the same, but as it is explained in the present description, adding the $C_6O_7H_8$ (citric acid) greatly strengthens the effectivness of the original solution. The composition also can add anise-flavored or lemon-flavored essence to help conceal the acid and sour taste of the composition for the reason of making it less unpleasant when being applied to the patient's teeth and oral cavity.

DESCRIPTION OF THE INVENTION

The embodiments disclosed herein are for the purpose of providing the required description of the present subject matter. They are only exemplary, and may be embodied in various forms. Therefore, specific details disclosed herein are not to be interpreted as limiting the subject matter as defined in the accompanying claims.

The characteristic details of the present invention are clearly shown in the accompanying description below.

Improvements to compositions and procedure for cleaning the enamel of teeth are as follows:

A 6N concentration of HCl in water, corresponding to 21 weight % weight hydrochloric acid q.p., in the composition (Tables 1 and 2), 6 weight % $C_6O_7H_8$, citric acid (Tables 1 and 2), 5 weight % lemon-flavored artificial liquid essence (Table 1), 0.2 weight % anise-flavored artificial liquid essence (Table 2), and 68% to 71% by weight water demineralised by reverse osmosis and bacterially purified by ozonisation (Table 1) or (Table 2), respectively. All percents are weight percents, based on the total weight of the composition.

The HCl composition, in such range (6N) (Tables 1 and 2), shows completely successful results; such composition reacts with positive ions, forming salts, property through which the teeth's enamel structure is cleaned without affecting it but only extracting the organic and inorganic substance ions which are occupying the spaces existing between the crystals not too calcified with fluoroapatite. This action is favorably strengthened when citric acid ($C_6O_7H_8$) is included in the composition at the approximate 6% (weight percent) level. (Tables 1 and 2). The citric acid ($C_6O_7H_8$) is an irrigating substance, classified as a chelating agent which due to its low pH reacts with metallic ions in the hydroxyapatite crystals for producing a metallic chelating agent which reacts with the chelating agent's end elements or groups when removing the calcium ions. When applying the improved solution for cleaning the enamel of teeth in the dental piece to be treated, the citric acid effect ($C_6O_7H_8$) is very fast, since it requires only thirty seconds after applying the 6% solution over the teeth enamel for dissolving the organic matter, which has been determined to serendipidously increase its effectiveness over the mottle stain, white, opaque or yellow stain. This occurs in a matter of seconds and permanently, very effectively addressing or removing the problems of brown pigmentation of teeth with mottled enamel or chronic endemic dental fluorosis, as well as white, opaque or yellow stains.

Since the composition of this invention is a colorless, slightly irritating, liquid and/or sour, lemon-flavored or anise-flavored essence can be added in order to eliminate acidity negatives of both HCl (hydrochloric acid), as well as $C_6O_7H_8$ (citric acid), and at the same time leaving a pleasant smell and freshness in the patient's mouth.

Application Procedure

After evaluating the patient, the procedure and application of the improved solution or composition for cleaning the enamel of teeth starts as follows:

With the patient sitting on the dental chair, first the dental pieces, items or teeth to be treated are isolated, one by one, generally as previously practiced, with the conventional rubber dam, placing an appropriate staple to the morphology of the dental piece and applying dental wax to the tooth's neck to perfectly seal the rubber dam and duly protect the lower teeth as well as the gingival mucosa and the rest of the oral cavity. Second, with a small cotton swab secured with snap clamps and previously impregnated with the composition of the present invention, the dental professional performs a firm circular rubbing motion until the brown stain of the mottle as well as the white, opaque and yellow stains are totally dissolved.

Immediately after dissolving the brown mottle, the white, opaque or yellow stains, on the treated dental piece a calcium hydroxide paste and water are applied to neutralize the excess composition. Finally, the mouth is rinsed with natural water to remove any calcium hydroxide paste residue.

It should be noted as additional information, that after treating with the improved solution for cleaning the enamel of the teeth, as time goes by, the person's saliva acts as a natural remineralizer and restructurer of the enamel of the teeth. This keeps the enamel in excellent condition for twenty years or longer.

Table 1 and Table 2 set out compositions of the improved solution for cleaning the enamel of teeth. These are used to make up one liter of the composition.

TABLE 1

| Hydrochloric acid 6N | HCl | 21.00 wt. % Optimum |
|---|---|---|
| Citric acid | $C_6O_7H_8$ | 6.00 wt. % Optimum |
| Lemon-flavored artificial liquid essence | | 5.00 wt. % Optimum |
| Demineralised water by reverse osmosis and bacterially purified | | 68.00 wt. % Optimum |
| | | 100.00 wt. % |

TABLE 2

| Hydrochloric acid 6N | HCl | 21.00 wt. % Optimum |
|---|---|---|
| Citric acid | $C_6O_7H_8$ | 6.00 wt. % Optimum |
| Anise-flavored artificial liquid essence | | 2.00 wt. % Optimum |
| Demineralised water by reverse osmosis and bacterially purified | | 71.00 wt. % Optimum |
| | | 100.00 wt. % |

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims.

The invention claimed is:

1. A composition that removes stains of chronic endemic dental fluorosis from the enamel of teeth, comprising: 6N concentration of hydrochloric acid (HCl), corresponding to approximately 21% hydrochloric acid q.p.; approximately 6% of citric acid ($C_6O_7H_8$); and a water component selected from the group consisting of approximately 5% of lemon-flavored artificial liquid essence and approximately 68% of demineralized water, prepared by reverse osmosis and bacterially purified by ozonisation, and approximately 2% of anise-flavored artificial liquid essence and approximately 71% of demineralized water, prepared by reverse osmosis and bacterially purified by ozonisation, all percentages being by weight and based on the total weight of the composition.

2. The composition according to claim 1, wherein the hydrochloric acid (HCl) and citric acid ($C_6O_7H_8$) are in aqueous solution.

3. The composition according to claim 1, wherein the hydrochloric acid (HCl), in aqueous solution, has a sole concentration of 6N, HCl in 100 ml of water.

4. Improvements to the composition according to claim 1, the improvement comprising combining citric acid ($C_6O_7H_8$) at 6% by weight with the 6N hydrochloric acid,in; the water component, wherein the improved composition removes stains of chronic endemic dental fluorosis from the enamel of teeth.

5. A process for applying the composition according to claim 1, comprising:

isolating a dental piece to be treated through the conventional rubber dam technique and applying dental wax to the neck of the tooth in order to seal the rubber dam and protect the lower teeth as well as the gingival mucosa and the rest of the oral cavity;

followed by applying the composition of claim 1 over the surface of the piece to be treated, the applying being with a small cotton swab secured with snap clamp;

performing a firm circular rubbing motion for between about thirty seconds and about one minute, until the stains disappear; and thereby removing stains of chronic endemic dental fluorosis from the enamel of the teeth.

6. The procedure process according to claim 5, wherein the removing step removes the stain that includes brown pigmentation as well as white, opaque and yellow stains of endemic dental fluorosis.

7. The composition according to claim 1, wherein the stains of endemic dental fluorosis include brown pigmentation as well as white, opaque and yellow stains.

* * * * *